United States Patent [19]

Aichinger et al.

[11] 4,455,669
[45] Jun. 19, 1984

[54] X-RAY DIAGNOSTIC INSTALLATION COMPRISING MEANS FOR THE FORMATION OF A TRANSPARENCY SIGNAL

[75] Inventors: Horst Aichinger, Fuerth; Heinz E. Kranberg, Erlangen, both of Fed. Rep. of Germany

[73] Assignee: Siemens Aktiengesellschaft, Berlin & Munich, Fed. Rep. of Germany

[21] Appl. No.: 230,638

[22] Filed: Feb. 2, 1981

[30] Foreign Application Priority Data

Mar. 4, 1980 [DE] Fed. Rep. of Germany ....... 3008261

[51] Int. Cl.³ .......................................... G03B 41/16
[52] U.S. Cl. .................................... 378/97; 378/157
[58] Field of Search .................... 378/97, 108, 157

[56] References Cited

U.S. PATENT DOCUMENTS

| 2,486,866 | 11/1949 | Morgan | 378/97 |
| 2,825,816 | 3/1958 | Rogers | 378/108 |
| 4,097,741 | 6/1978 | Pfeeler | 378/97 |
| 4,189,645 | 2/1980 | Chaney | 378/157 |

Primary Examiner—Craig E. Church
Attorney, Agent, or Firm—Hill, Van Santen, Steadman & Simpson

[57] ABSTRACT

In an exemplary embodiment, two radiation detectors are arranged behind the radiography subject. One of the detectors is covered by a radiation filter. A different radiation attenuation along the radiation paths of the respective detectors thereby takes place, so that, through division of the output signals of the detectors, a quotient signal can be obtained which corresponds to the radiation transparency of the radiography subject.

1 Claim, 1 Drawing Figure

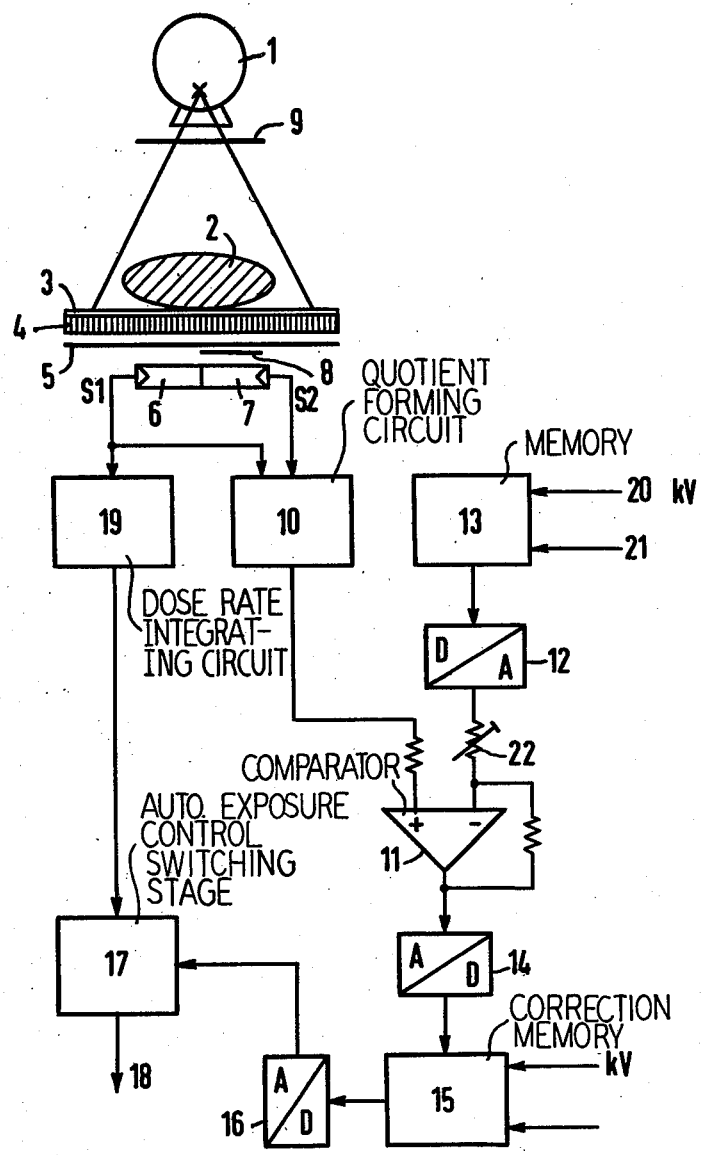

X-RAY DIAGNOSTIC INSTALLATION COMPRISING MEANS FOR THE FORMATION OF A TRANSPARENCY SIGNAL

BACKGROUND OF THE INVENTION

The invention relates to an x-ray diagnostic installation comprising means for the formation of an electric signal which corresponds to the radiation transparency of the radiography subject.

In x-ray diagnostics it is important to know the radiation transparency of the patient in order to be able to prepare optimally blackened (or dense) radiographs. In the case of utilization of an x-ray automatic exposure control which automatically terminates a radiograph when a predetermined radiation dose has acted upon the x-ray film, the disconnection (or switch-off) dose, as determined by means of the switching stage of the automatic exposure timer, is dependent, due to the dependency of the sensitivity of the detector upon the radiation quality, not only upon the selected x-ray tube voltage, but, in the case of a given subject thickness, is also dependent upon the radiation transparency of the radiography subject. This dependency is accounted for in that intensifier foils are employed in conjunction with the x-ray film, which foils absorb a large portion of the x-radiation and in that the radiation measuring chamber of the automatic exposure timer is arranged behind the cassette with the x-ray film and the intensifier foils. Due to the hardening through the radiography subject, the absorption of the x-radiation by the intensifier foils, in addition to being dependent upon the x-ray tube voltage, in the case of a given subject thickness, is also dependent upon the radiation transparency of the radiography subject. Accordingly, it would be necessary to supply to the switching stage of the automatic exposure timer, for a precise exposure, information regarding the subject thickness as well as information regarding the radiation transparency of the radiography subject, which codetermine the optimum disconnection (or switch-off) dose value. The described difficulties can, indeed, be avoided if the radiation detector of the automatic exposure control is arranged in front of the photographic exposure system; in this case, however, a shadow-free radiation detector must be employed. In addition, as compared with the arrangement of the radiation detector behind the photographic exposure system, a somewhat enlarged subject-to-film distance and an increased prefiltering of the image-producing radiation results.

SUMMARY OF THE INVENTION

The object underlying the invention resides in creating an x-ray diagnostic installation of the type initially cited in which, in a simple fashion, a signal corresponding to the subject thickness and radiation transparency of the radiography subject can be formed which thus represents information regarding the subject thickness and density.

In accordance with the invention, this object is achieved in that two radiation detectors, to be arranged behind the radiography subject, are provided, that filter means are present which provide different radiation attenuation along the radiation paths of the respective detectors, and that the detectors are connected to a quotient formation element which forms the quotient of the detector output signals. In the inventive x-ray diagnostic installation, the x-radiation to the two radiation detectors is differently filtered by interposed filters, so that the quotient signal based on the detector output signals is a measure of the thickness and radiation transparency of the radiography subject. This quotient signal does, indeed, also depend upon other exposure values; in particular, upon the x-ray tube voltage; however, these exposure values are known, so that, with the aid of calibration values, it is possible to infer from the quotient signal, the subject thickness and radiation transparency of the radiography subject.

The output signal of the quotient formation element can control the switching stage of an x-ray automatic exposure control with the objective of setting the disconnection dose value in dependence upon the thickness and radiation transparency of the patient. In this instance, it is possible, while utilizing intensifier foils in conjunction with an x-ray film, to automatically take into account the radiation absorption—caused by the intensifier foils, but dependent upon the radiation transparency of the radiography subject—with the radiation detector of the automatic exposure control arranged, viewed in radiation direction, behind the film cassette.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWING

The single FIGURE is a diagrammatic view of an x-ray diagnostic installation, showing an associated electric circuit for controlling a radiographic exposure, responsive to an actual measurement of radiation transparency of the patient.

DETAILED DESCRIPTION

In the drawing an x-ray tube 1 is illustrated which irradiates a patient 2 resting on a support plate 3. Viewed in radiation direction, a secondary radiation grid 4 as well as a film-foil system 5 is disposed behind the support plate 3. Two radiation detectors 6 and 7 are adjacently arranged behind the film-foil system 5. However, the radiation detectors can also be arranged in tandem. In front of the radiation detector 7 a radiation filter 8 is disposed; e.g. a thin copper foil. In addition, in the path of primary radiation in front of the patient 2, another radiation filter 9 e.g. an aluminum plate, is arranged.

The output signals S1 and S2 of the detectors 6 and 7 are supplied to a quotient forming circuit 10 whose output signal is compared in a comparator 11 with calibration information for a standard thickness and density which has been taken from a memory 13 via a digital-to-analog converter 12. The output signal of the comparator 11, which corresponds to the difference between its input signals, is supplied via an analog-to-digital converter 14 to a correction memory 15 which delivers a correction signal for every difference signal. The resulting output information of the correction memory 15 codetermines the disconnection dose value of an automatic x-ray exposure control and is therefore supplied, via a digital-to-analog converter 16, to a switching stage 17 of an automatic exposure control which delivers at its output 18 a disconnect signal when a predetermined radiation dose value at the x-ray film has been attained.

The automatic exposure control additionally contains an integration stage 19.

In the memory 13, for all provided exposure values, the transparency data, associated with a mean radiation transparency and thickness, are stored. The call-up of the respectively required value proceeds via signals at the inputs 20 and 21, whereby a signal is connected to the input 20 which corresponds to the selected x-ray tube voltage, and a signal is connected to the input 21 which corresponds to the selected filter 8. The values present in the memory 13 were previously ascertained (or determined) with a calibration measurement. The adaptation to the different film-foil systems 5 proceeds by means of information which is supplied via a series resistance 22 of the comparator 11 and which correspondingly influences the amplification of the comparator 11 designed as a differential amplifier.

The output signal of the digital-to-analog converter 16, which has been formed from the difference signal between the actual radiation transparency and the mean radiation transparency in the case of the selected exposure values, influences the nominal setpoint value of the disconnection dose in dependence upon the actual radiation transparency of the radiography subject.

It must be borne in mind that, with the aid of the two detectors 6 and 7, disposed adjacent one another in the illustrated exemplary embodiment, of which one is covered by the filter 8, a signal is formed which corresponds to the actual transparency and thickness of the radiography subject, and that this signal controls the automatic exposure timer with the objective of determining an optimum setpoint value of the disconnection dose. The illustrated x-ray diagnostic installation is particularly suited for mammography photographs which a soft x-radiation with x-ray tube voltages of between 25 and 40 kV is employed, because varying transparencies of the radiography subject, pursuant to utilization of varying film-foil systems, have a particularly strong effect therein on the disconnection dose value respectively required.

In the illustrated exemplary embodiment, a radiation filter 8 is arranged in front of one of the detectors; namely, in front of the detector 7, whereas a corresponding filter in front of the detector 6 is lacking. What is achieved thereby is that, along the radiation paths of the detectors 6, 7, a different radiation attenuation occurs, so that, from the detector output signals, the radiation transparency and thickness of the radiography subject can be determined.

It will be apparent that many modifications and variations may be effected without departing from the scope of the novel concepts and teachings of the present invention.

SUPPLEMENTARY DISCUSSION

For the case where the radiation detectors are arranged in tandem along the radiation path behind the film-foil system 5 (with filter 8 omitted), a first detector may have an area and location corresponding to detectors 6 and 7 and supply a detector output signal S1' to components 10 and 19. Behind the first detector, a filter may be located having an area corresponding to the area of the first detector. A second detector of the same area as the first detector may then be located behind the filter, so that the second detector receives only radiation which has passed through the first detector and the filter. The second detector would then be generally analogous to detector 7 which receives radiation only via filter 8, and would supply a detector output signal S2' to component 10.

We claim as our invention:

1. An x-ray diagnostic installation comprising an x-ray tube for producing radiation at a location for receiving a radiography subject (2), an x-ray tube power supply for supplying operating power to the x-ray tube, an x-ray image means (5) for disposition behind the location for receiving a radiography subject (2) for recording a radiation image, an exposure terminating switch for effecting a termination of an x-ray exposure operation of said x-ray tube, means for the formation of an electric signal which corresponds to the radiation transparency of the radiography subject, said means comprising two radiation detectors (6, 7) arranged in respective radiation paths behind the location for receiving a radiography subject (2) for supplying detector output signals, filter means (8) being present for providing a different radiation attenuation along the respective radiation paths of the respective detectors (6, 7), and a quotient forming circuit (10) connected with said radiation detectors (6, 7) for forming a quotient of said detector output signals as said electric signal, the detectors (6, 7) being disposed adjacent one another, and said filter means comprising a radiation filter (8) arranged in front of one of the detectors (7), an automatic exposure control circuit controlling said exposure terminating switch and comprising a switching stage (17) for actuation to effect termination of an x-ray exposure operation, said quotient forming circuit being disconnection dose value, in dependence upon the radiation transparency and thickness of the radiography subject, a memory (13) for storing information associated with a mean radiation transparency and specific exposure values, a comparator (11) whose inputs are coupled with said memory and with the quotient forming circuit (10) for comparing the information of the memory (13) which information corresponds to the selected exposure values with the electric signal from said quotient forming circuit and a correction memory (15) connected with the output of the comparator (11) such that the correction memory (15) supplies a correction value to said switching stage in accordance with the difference signal supplied to the correction memory by said comparator as a function of the x-ray tube high voltage.

* * * * *